(12) United States Patent
Clark et al.

(10) Patent No.: US 11,351,009 B2
(45) Date of Patent: Jun. 7, 2022

(54) DENTAL COMPOSITE CAPSULE FOR INJECTION MOLDED FILING TECHNIQUES

(71) Applicant: David J. Clark, Tacoma, WA (US)

(72) Inventors: David J. Clark, Tacoma, WA (US); Jeremy Henderson, Tacoma, WA (US)

( * ) Notice: Subject to any disclaimer, the term of this patent is extended or adjusted under 35 U.S.C. 154(b) by 305 days.

(21) Appl. No.: 15/533,220

(22) PCT Filed: Dec. 4, 2015

(86) PCT No.: PCT/US2015/063993
§ 371 (c)(1),
(2) Date: Jun. 5, 2017

(87) PCT Pub. No.: WO2016/090246
PCT Pub. Date: Jun. 9, 2016

(65) Prior Publication Data
US 2018/0256293 A1  Sep. 13, 2018

Related U.S. Application Data (60) Provisional application No. 62/087,534, filed on Dec. 4, 2014.

(51) Int. Cl.
| | |
|---|---|
| *A61C 5/66* | (2017.01) |
| *A61C 5/62* | (2017.01) |
| *A61C 5/64* | (2017.01) |
| *A61K 6/887* | (2020.01) |

(52) U.S. Cl.
CPC .................. *A61C 5/66* (2017.02); *A61C 5/62* (2017.02); *A61C 5/64* (2017.02); *A61K 6/887* (2020.01)

(58) Field of Classification Search
CPC ... A61C 5/60–68; A61C 19/08; A61C 9/0026; B05C 17/00553; B05C 17/00559; B05C 17/00563; B05C 17/0596; A61B 2017/00495; A61B 17/00491; A61M 2005/1787; A61M 5/19; B01F 15/0441–045
USPC .............................................. 141/9
See application file for complete search history.

(56) References Cited

U.S. PATENT DOCUMENTS

| | | | |
|---|---|---|---|
| 3,595,439 A | 7/1971 | Newby et al. | |
| 4,340,529 A | 7/1982 | Lee, Jr. et al. | |
| 4,957,441 A * | 9/1990 | Bryan | A61C 5/00 433/228.1 |
| 4,995,540 A * | 2/1991 | Colin | A61C 9/0026 222/132 |
| 5,547,379 A * | 8/1996 | Hasel | A61C 5/00 433/212.1 |

(Continued)

FOREIGN PATENT DOCUMENTS

| | | | | |
|---|---|---|---|---|
| DE | 19638067 A1 * | 3/1998 | ............. | A61K 6/083 |
| EP | 0974320 A1 * | 1/2000 | ............. | A61M 5/178 |

OTHER PUBLICATIONS

The International Search Report and Written Opinion dated Feb. 12, 2016, for International Application PCT/US2015/063993.

*Primary Examiner* — Jacqueline T Johanas
*Assistant Examiner* — Shannel Nicole Belk
(74) *Attorney, Agent, or Firm* — Quarles & Brady LLP (57) ABSTRACT

The present invention relates to methods for the restoration of a decayed portion of a tooth or re-restoration of a previously filled tooth, and to dental capsules and dental composite resin dispensers that may be used in the methods for the restoration of a decayed portion of a tooth.

22 Claims, 8 Drawing Sheets

(56) References Cited

U.S. PATENT DOCUMENTS

| | | | |
|---|---|---|---|
| 6,089,407 A | 7/2000 | Gardos | |
| 6,261,094 B1 * | 7/2001 | Dragan | A61C 5/66 |
| | | | 433/90 |
| 6,379,152 B1 | 4/2002 | Dragan | |
| 7,303,392 B1 | 12/2007 | Schermerhorn et al. | |
| 2003/0153903 A1 | 8/2003 | Kumagi et al. | |
| 2007/0250013 A1 * | 10/2007 | Brennan | A61B 17/00491 |
| | | | 604/191 |
| 2007/0272567 A1 * | 11/2007 | Peuker | A61C 5/62 |
| | | | 206/219 |
| 2008/0144426 A1 * | 6/2008 | Janssen | B01F 7/00216 |
| | | | 366/130 |
| 2009/0191506 A1 * | 7/2009 | Clark | A61C 5/50 |
| | | | 433/41 |
| 2010/0206905 A1 | 8/2010 | Horner et al. | |
| 2010/0240004 A1 * | 9/2010 | Zalsman | A61C 5/62 |
| | | | 433/90 |
| 2016/0030299 A1 * | 2/2016 | Sadakane | A61K 6/0073 |
| | | | 523/116 |
| 2017/0000585 A1 * | 1/2017 | Barg | A61C 5/64 |

* cited by examiner

Fig. 11

DENTAL COMPOSITE CAPSULE FOR INJECTION MOLDED FILING TECHNIQUES

CROSS-REFERENCES TO RELATED APPLICATIONS

This application is a 371 application of PCT/US2015/063993 filed Dec. 4, 2015 which claims priority from U.S. Patent Application No. 62/087,534 filed Dec. 4, 2014.

STATEMENT REGARDING FEDERALLY SPONSORED RESEARCH

Not Applicable.

BACKGROUND OF THE INVENTION

1. Field of the Invention

The present invention relates to methods for the restoration of a decayed portion of a tooth or re-restoration of a previously filled tooth, and to composite resin dispensers and capsules that may be used in the methods for the restoration of a decayed portion of a tooth.

2. Description of the Related Art

Dental cavities that have spread to the dentin or have undergone cavitation are typically treated by removing the decayed portion of the tooth and thereafter filling the missing tooth structure with a restorative material such as silver (amalgam), white (resin), porcelain, or gold. Cavities that are located adjacent to neighboring teeth are called interproximal cavities.

When treating interproximal cavities, the dentist first removes the decayed portion of the side of the tooth. In order to properly deposit the restorative material on the side of the tooth without undesired leaking of the restorative material beyond the side of the tooth, the dentist places a dental matrix around at least a portion of the tooth. The dental matrix may be a metallic or plastic strip, and when the matrix is placed around at least a portion of the tooth, the matrix acts as a form for the desired shape of the restored tooth.

The Bioclear® brand matrix (available at http://www.bioclearmatrix.com) has advanced dental restoration with an injection molding process (see U.S. Patent Application Publication No. 2008/0064012). Even with these advancements, there is still a need for further advancements in methods and devices for the restoration of a decayed portion of a tooth.

SUMMARY OF THE INVENTION

The invention meets the foregoing needs by providing improved dental capsules and dental composite dispensers for the restoration of a decayed portion of a tooth.

An aspect of the invention is a preloaded body (e.g., a capsule) that is designed to be used in conjunction with unheated extrusion or heated extrusion from a dental composite dispenser. A first composite resin and a second composite resin are preloaded in the interior space of the body. In one embodiment, the first composite resin has a first viscosity, and the second composite resin has a second viscosity less than the first viscosity. In another embodiment, the first composite resin has a first color, and the second composite resin has a second color different from the first color. In another embodiment, the first composite resin has a first opacity, and the second composite resin has a second opacity different from the first opacity. In another embodiment, a first volume percentage of a first filler in the first composite resin is greater than a second volume percentage of a second filler in the second composite resin. Preferably, the capsule is a single use, disposable capsule.

In the capsule, the first composite resin can be paste composite, and the second composite resin can be flowable composite. In the capsule, the first composite resin can be a bulk fill paste composite, and the second composite resin can be bulk fill flowable composite. A bulk-fill composite can be a light-curable and nano-hybrid composite including a prepolymer shrinkage stress-relieving filling technology, a light-initiator/polymerization booster, and a light-sensitivity filter that make the bulk-fill composite beneficial for bulk placement in increments up to four millimeters. In the capsule, the first composite resin can be a resin modified glass ionomer composite, and the second composite resin can be a resin modified glass ionomer composite. A resin modified glass ionomer composite may include an aqueous polyalkenoic acid (e.g., polyacrylic acid), a glass component (e.g., a fluoroaluminosilicate), hydroxyethylmethacrylate, and a photoinitiator.

In another embodiment, a light-curable resin tooth bonding agent is preloaded in the interior space of the body between the second composite resin and a dispensing orifice of the body. A frangible barrier may be positioned in the interior space of the body between the second composite resin and the light-curable resin tooth bonding agent.

Another aspect of the invention is a capsule for use in a dental composite dispenser. The capsule includes a hollow body comprising a wall defining an interior space of the body. The body has a proximal end and a distal end having a dispensing orifice. A composite resin is positioned in the interior space of the body. The composite resin has a viscosity gradient in which viscosity increases from the distal end of the body to the proximal end of the body. Non-limiting example viscosity gradients include a gradient comprising 2, or 3, or 4, or 5, or 6, or 7, or 8, or 9, or 10, or 11 or more contiguous resins, each resin in the lineup from the distal end of the body to the proximal end of the body being of increased viscosity.

Thus, the invention includes the manufacture and placement of flowable composite dental filling material and/or paste composite dental filling material into preloaded unidose type capsules. The capsules may possess reduced tip orifice size through which the extrusion of the flowable composite and the paste composite through the smaller dispensing orifice is dependent on alteration of the physical characteristics of the paste composite from heat and/or extreme pressure or other means by which the physical properties of the paste composite are altered to allow increased flowability (such as vibration, ultrasonic energy, microwaves, or similar physical and thermal energies). The small dispensing orifice with a reduced tip orifice size allows for: (i) the direct placement into cavities that are smaller than the circumference of traditional paste capsule tip orifice size, (ii) an injection molded composite technique which requires deeper insertion of the capsule tip into the cavity preparation, and (3) use with anatomic and pre-curved matrices that impede the insertion of larger, traditional tip orifices.

The features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

The invention provides improved methods and dental composite capsules for the restoration of a decayed portion of a tooth.

In an example method according to the invention for the restoration of a tooth, the dentist locates a tooth having a cavity. A hollow cavity preparation is prepared in a tooth. The tools and techniques for forming the hollow cavity preparation are well known in the art and therefore will not be explained further.

In order to properly deposit the restorative material on the tooth without undesired leaking of the restorative material beyond the tooth, the dentist may place a dental matrix around at least a portion of the tooth. A sectional anatomic translucent dental matrix may be placed on the tooth. When the matrix is placed around at least a portion of the tooth, the matrix acts as a form for the desired shape of the restored tooth.

The cavity preparation in the tooth is then etched with liquid and/or gel phosphoric acid. The cavity preparation in the tooth is then rinsed and dried. A lightly filled or unfilled light curable resin tooth bonding agent is then applied to the tooth covering the entire cavity preparation. The resin tooth bonding agent is not light cured at this point. Resin tooth bonding agents improve composite to enamel and/or dentin bonding.

A light curable flowable composite resin is then injected from a dental capsule according to the invention directly into the pool of resin tooth bonding agent. The light curable flowable composite and resin tooth bonding agent are not light cured at this point. Generally, light curable flowable composite resins contain 20-25 percent less filler in the light curable polymeric material than nonflowable paste materials. Light curable resins are preferred as light cured resins are more color stable than chemically cured resins.

A light curable paste composite resin is then extruded from the same dental capsule according to the invention into the pool of flowable composite resin and resin tooth bonding agent. The next steps are burnishing, carving the anatomy and carving excess composite. There is no need to use a condenser or plugger.

The filled cavity preparation is then cured using a curing light such as high intensity light emitting diode (LED) lights, plasma-arc curing lights, halogen lights, and laser lights. The matrix is then removed, and the restored tooth is polished with discs, strips, and rubber tipped and carbide burs.

One version of the invention provides a capsule for use in a dental composite dispenser. The capsule includes: (i) a hollow body comprising a wall defining an interior space of the body, wherein the body includes a proximal end and a distal end having a dispensing orifice; a first composite resin positioned in the interior space of the body; and a second composite resin positioned in the interior space of the body. The first composite resin has a first viscosity, and the second composite resin has a second viscosity less than the first viscosity.

Another version of the invention provides a capsule for use in a dental composite dispenser. The capsule includes: (i) a hollow body comprising a wall defining an interior space of the body wherein the body includes a proximal end and a distal end having a dispensing orifice; (ii) a first composite resin positioned in the interior space of the body; and (iii) a second composite resin positioned in the interior space of the body. The first composite resin has a first color, and the second composite resin has a second color different from the first color.

Another version of the invention provides a capsule for use in a dental composite dispenser. The capsule includes: (i) a hollow body comprising a wall defining an interior space of the body wherein the body includes a proximal end and a distal end having a dispensing orifice; (ii) a first composite resin positioned in the interior space of the body; and (iii) a second composite resin positioned in the interior space of the body. The first composite resin has a first opacity, and the second composite resin has a second opacity different from the first opacity.

Another version of the invention provides a capsule for use in a dental composite dispenser. The capsule includes: (i) a hollow body comprising a wall defining an interior space of the body, the body including a proximal end and a distal end having a dispensing orifice; (ii) a first composite resin positioned in the interior space of the body; and (iii) a second composite resin positioned in the interior space of the body. The first composite resin comprises a first filler and a light curable resin, and the second composite resin comprises a second filler and light curable resin, and a first volume percentage of the first filler in the first composite resin is greater than a second volume percentage of the second filler in the second composite resin.

In any of these versions of the capsule, the second composite resin can be positioned between the first composite resin and the dispensing orifice, and a plunger can be positioned between the first composite resin and the proximal end of the body. In any of these versions of the capsule, the first composite resin and the second composite resin can be in contact before use of the capsule in the dental composite dispenser. No barrier need be positioned between the first composite resin and the second composite resin.

In any of these versions of the capsule, the first composite resin can be a paste composite, and the second composite resin can be a flowable composite. The first composite resin can comprise from about 1% by volume to about 99% by volume of the interior space of the body, and the second composite resin can comprise from about 1% by volume to about 99% by volume of the interior space of the body. The first composite resin can comprise from about 25% by volume to about 99% by volume of the interior space of the body, and the second composite resin can comprise from about 1% by volume to about 75% by volume of the interior space of the body. The first composite resin can comprise from about 50% by volume to about 99% by volume of the interior space of the body, and the second composite resin can comprise from about 1% by volume to about 50% by volume of the interior space of the body. The first composite resin can comprise from about 65% by volume to about 85% by volume of the interior space of the body, and the second composite resin can comprise from about 15% by volume to about 35% by volume of the interior space of the body.

In any of these versions of the capsule, the first composite resin and the second composite resin can be essentially not mixed before exiting the dispensing orifice. Alternatively, less than about 5% by volume of the first composite resin and less than about 5% by volume of the second composite resin are mixed before exiting the dispensing orifice. Alternatively, less than about 10% by volume of the first composite resin and less than about 10% by volume of the second composite resin are mixed before exiting the dispensing orifice.

In any of these versions of the capsule, a light-curable resin tooth bonding agent can be positioned in the interior space of the body between the second composite resin and the dispensing orifice. A frangible barrier can be positioned in the interior space of the body between the second composite resin and the light-curable resin tooth bonding agent.

In any of these versions of the capsule, the first composite resin is a paste composite, and the viscosity of the first composite resin can be lowered by heating. An amount of second filler in the second composite resin can be 20 to 25 percent less than an amount of first filler in the first composite resin. The first composite resin can be a bulk fill paste composite, and the second composite resin can be a bulk fill flowable composite. The first composite resin can be a resin modified glass ionomer composite, and the second composite resin can be a resin modified glass ionomer composite. In any of these versions of the capsule, the capsule is a single use, disposable capsule.

Another version of the invention provides a dental composite dispenser comprising a housing including an end section for dispensing composite; and one of any of the versions of the capsule in the end section of the housing. The dispenser can comprise an electrical power supply; and at least one resistive heating element in electrical communication with the power supply, wherein each heating element is located in the end section of the housing. The dispenser can comprise a movable piston engaging the inner surface of the body, wherein movement of the piston toward the dispensing orifice sequentially extrudes the second composite resin and the first composite resin from the dispensing orifice.

Another version of the invention provides a method for the restoration of a tooth. The method includes the steps of: (a) removing a portion of the tooth to form a cavity preparation; (b) sequentially extruding the second composite resin and the first composite resin into the cavity preparation from the dispensing orifice of one of any of the versions of the capsule; and (c) simultaneously light curing the second composite resin and the first composite resin contained in the cavity preparation. The method can further comprise placing a light-curable resin tooth bonding agent into the cavity preparation. The method can further comprise surrounding the cavity preparation with a matrix. The method can include the step of loading the capsule into an end section of a housing of a dental composite dispenser and sequentially extruding the second composite resin and the first composite resin from the dispensing orifice of the capsule.

In the method, the dental composite dispenser can comprise an electrical power supply, and at least one resistive heating element in electrical communication with the power supply wherein each heating element is located in the end section of the housing. The dental composite dispenser can comprise a movable piston engaging the inner surface of the body, and movement of the piston toward the dispensing orifice sequentially extrudes the second composite resin and the first composite resin from the dispensing orifice. The method can include the step of extruding a light-curable resin tooth bonding agent from the capsule into the cavity preparation. The method can include the step of extruding a light-curable resin tooth bonding agent from the capsule into the cavity preparation and breaking a frangible barrier positioned in the interior space of the body between the second composite resin and the light-curable resin tooth bonding agent. The method can include the step of extruding a light-curable resin tooth bonding agent from a second capsule into the cavity preparation. In the method, movement of a second piston of the dental composite dispenser toward a dispensing orifice of the second capsule extrudes the light-curable resin tooth bonding agent from the dispensing orifice of the second capsule.

Another version of the invention provides a capsule for use in a dental composite dispenser. The capsule includes (i) a hollow body comprising a wall defining an interior space of the body wherein the body includes a proximal end and a distal end having a dispensing orifice; and (ii) a composite resin positioned in the interior space of the body wherein the composite resin has a viscosity gradient in which viscosity increases from the distal end of the body to the proximal end of the body. One version of the invention provides a dental composite dispenser comprising a housing including an end section for dispensing composite; and a capsule with composite resin having a viscosity gradient, wherein the capsule is in the end section of the housing. The dispenser can comprise an electrical power supply; and at least one resistive heating element in electrical communication with the power supply, wherein each heating element is located in the end section of the housing. The dispenser can comprise a movable piston engaging the inner surface of the body, wherein movement of the piston toward the dispensing orifice sequentially extrudes the second composite resin and the first composite resin from the dispensing orifice. The invention provides a method for the restoration of a tooth. The method includes the steps of (a) removing a portion of the tooth to form a cavity preparation; (b) extruding composite resin into the cavity preparation from the dispensing orifice of a capsule with composite resin having a viscosity gradient; and (c) light curing the composite resin contained in the cavity preparation.

Another version of the invention provides a dental composite dispenser comprising: (i) a housing; (ii) a hollow chamber in the housing wherein the chamber comprises a wall defining an interior space of the chamber and the chamber includes a proximal end and a distal end having a dispensing orifice; (ii) a first reservoir containing a first composite resin wherein the first reservoir is in fluid communication with the interior space of the chamber; and (iv) a second reservoir containing a second composite resin wherein the second reservoir is in fluid communication with the interior space of the chamber. The dispenser can comprise a movable piston engaging a inner surface of the wall, wherein movement of the piston toward the dispensing orifice sequentially extrudes the second composite resin and the first composite resin from the dispensing orifice. The first reservoir can be in fluid communication with the proximal end of the chamber, and the second reservoir can be in fluid communication with the distal end of the chamber. The dispenser can comprise a first pump for moving the first composite resin from the first reservoir to the proximal end of the chamber, and a second pump for moving the second composite resin from the second reservoir to the distal end of the chamber. The dispenser can comprise a first switch on the housing for activating the first pump, and a second switch on the housing for activating the second pump. The dispenser can comprise a first one-way valve in fluid communication with the first reservoir and the chamber wherein the first one-way valve prevents flow from the chamber back to the first reservoir, and a second one-way valve in fluid communication with the second reservoir and the chamber wherein the second one-way valve prevents flow from the chamber back to the second reservoir.

Figure 1:
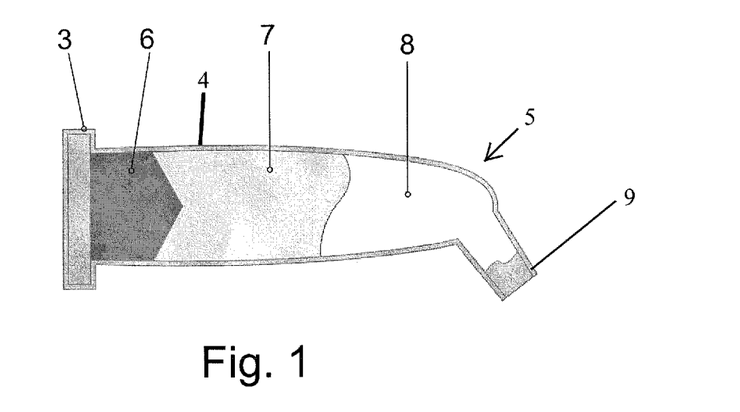
FIG. 1 shows a vertical cross-sectional view of a dental capsule according to one embodiment of the invention.

Turning now to FIG. 1, there is shown a dental capsule 3 according to one non-limiting embodiment of the invention. The capsule 3 has a wall 4 defining a hollow body 5. An interior space of the body 5 contains a plunger 6 in contact with a high viscosity dental composite resin 7, which is in contact with a lower viscosity composite resin 8, which is adjacent a dispensing orifice 9. The composite resins 7, 8 may have different opacities. The composite resins 7, 8 may have different colors. The composite resins 7, 8 may be in contact before use of the capsule 3 in a dental composite dispenser as no barrier need be positioned between the resin 7 and the resin 8.

Figure 2:
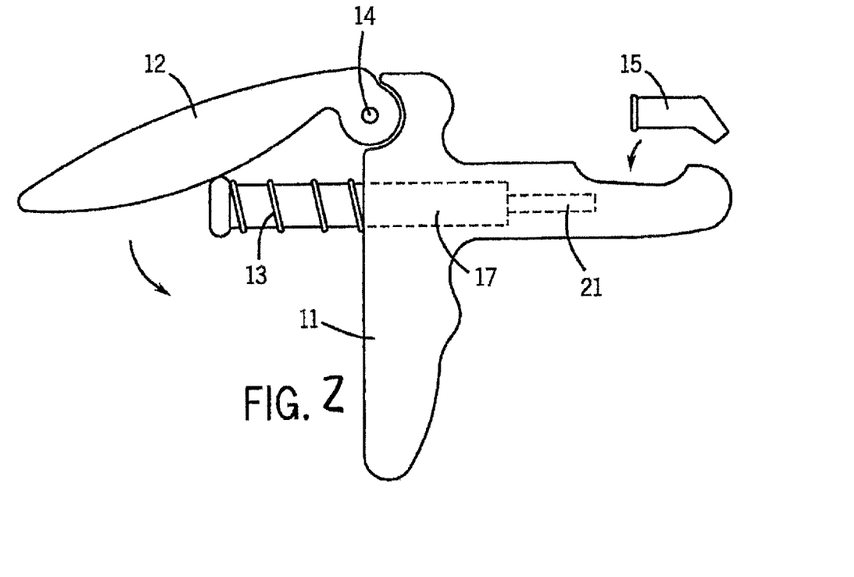
FIG. 2 is a side view of a composite delivery gun and yet to be inserted capsule according to the invention in which composite resin filling materials are pre-loaded.
Figure 3:
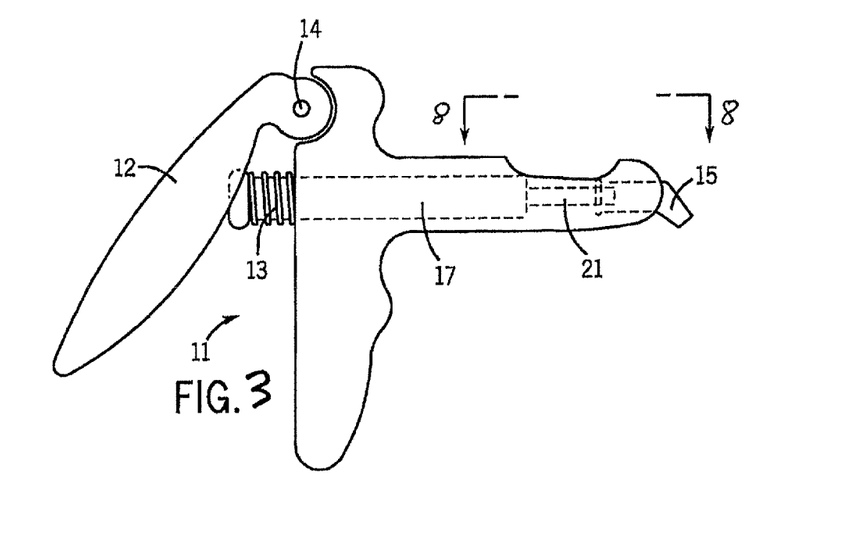
FIG. 3 shows the capsule inserted into the delivery gun of FIG. 2 and ready for expressing into a cavity preparation.

In FIGS. 2 and 3, there is shown a non-limiting example dental composite dispenser for use with the invention. FIG. 2 shows a side view of a dental composite dispenser gun 11 and a yet to be inserted capsule 15 in which two resin composite filling materials are pre-loaded. FIG. 3 shows the capsule 15 inserted into the dispenser gun 11 and ready for expressing into a cavity preparation. The piston 17 drives the rubber plunger 21 which in turn presses the composite resin filling materials. The handle 12 of the dispenser gun 11 in FIG. 3 has been pressed and is compressing the spring 13. Hinge 14 allows rotation of the handle 12 to press the piston 17.

Figure 4:
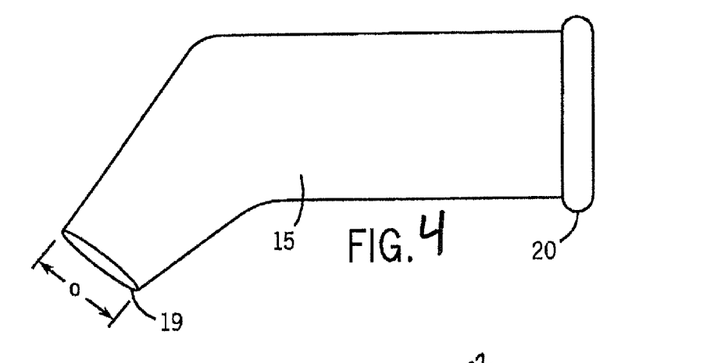
FIG. 4 is an enlarged side view of the capsule of FIG. 2.
Figure 5:
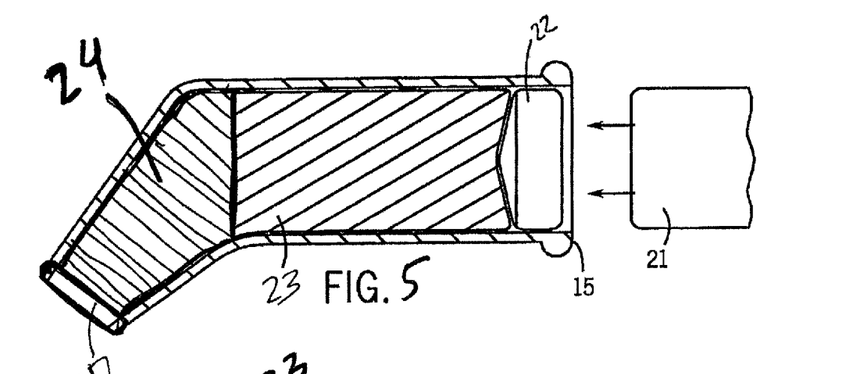
FIG. 5 is a vertical cross-sectional view of the capsule of FIG. 2 showing the position of plunger and the pre-loaded composite resin filling materials.
Figure 6:
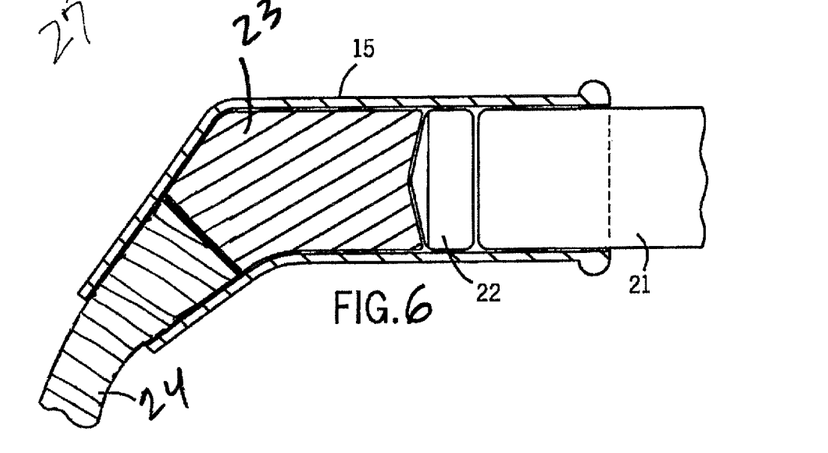
FIG. 6 is a vertical cross-sectional view of the capsule of FIG. 2 showing the extrusion of the composite resin filling materials.

FIG. 4 is a side view, close up of the capsule 15 having a dispensing orifice 19 with inside diameter O (which can be 2.5 millimeters) and a proximal end 20. FIG. 5 is a cross-sectional view of the capsule 15 showing the position of plunger 21 of the dispenser gun 11 and a pre-loaded first (paste) composite resin filling material 23 and second (flowable) composite resin filling material 24 which both move forward by way of a rear sliding disc 22 which is contacted by the plunger 21 of the dispenser gun 11. An end cap 27 covers the dispensing orifice 19 before use of the capsule 15. FIG. 6 shows the extrusion of the second (flowable) composite resin filling material 24 as the plunger 21 is driven into the barrel of the capsule 15 and pressure is applied to the first (paste) composite resin material 23 which thereby applies pressure to the second (flowable) composite resin filling material 24. Thus, the second (flowable) composite resin filling material 24 and the first (paste) composite resin composite material 23 are sequentially extruded from the capsule 15.

Figure 7:
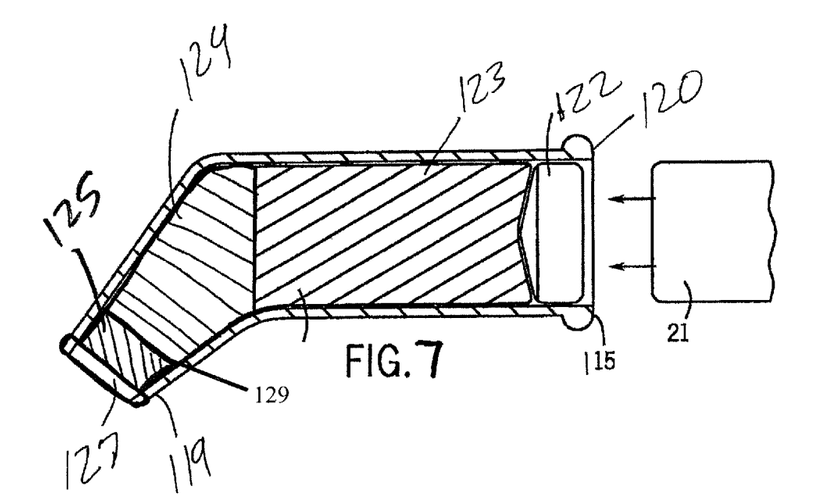
FIG. 7 is a vertical cross-sectional view of another capsule according to the invention showing the position of plunger and the pre-loaded composite resin filling materials.

FIG. 7 shows a cross-sectional side view of another non-limiting example dental capsule 115 for use with the invention. The capsule 115 has a dispensing orifice 119 with inside diameter O (which can be 2.5 millimeters) and a proximal end 120. The view of the capsule 115 shows the position of plunger 21 of the dispenser gun 11 and the pre-loaded first (paste) composite resin composite filling material 123 and second (flowable) composite resin filling material 124 and light curable resin tooth bonding agent 125 which all move forward by way of a rear sliding disc 122 which is contacted by the plunger 21 of the dispenser gun 11. An end cap 127 covers the dispensing orifice 119 before use of the capsule 115. The plunger 21 is driven into the barrel of the capsule 115 and pressure is applied to the first (paste) composite resin material 123 which thereby applies pressure to the second (flowable) composite resin filling material 124, which thereby applies pressure to the light curable resin tooth bonding agent 125. Thus, the light curable resin tooth bonding agent 125 and the second (flowable) composite resin filling material 124 and the first (paste) composite resin material 123 are sequentially extruded from the capsule 115. Optionally, a frangible barrier 129 is positioned in the interior space of the capsule 115 between the second (flowable) composite resin filling material 124 and the light-curable resin tooth bonding agent 125 to keep these materials separate until use. The frangible barrier 129 breaks open when the first (paste) composite resin material 123 applies pressure to the second (flowable) composite resin filling material 124 which thereby breaks open the frangible barrier 129.

Figure 8:
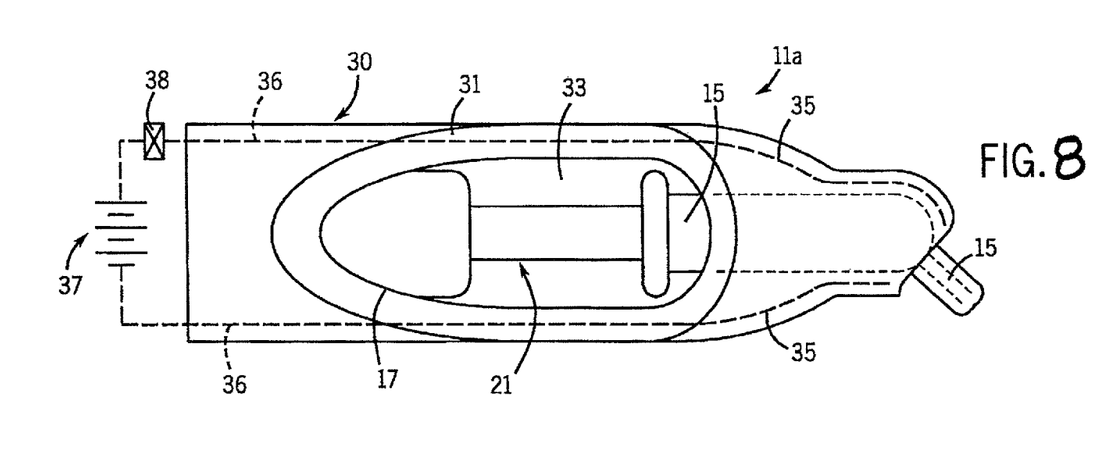
FIG. 8 shows a view taken along lines 8-8 of FIG. 3 showing one version of a composite dispenser having means for heating the capsule of FIGS. 4-6 or the capsule of FIG. 7.

Turning now to FIG. 8, there is shown another non-limiting example dental composite dispenser 11a according to the invention. The dental composite dispenser 11a includes an end section 30 for dispensing the resins from the capsule 15. The piston 17 drives a rubber plunger 21 which in turn presses the resin materials from the capsule 15 as described above for dispenser 11. The end section 30 has an opening 31 defining a space 33 in which the capsule 15 may be inserted into place as shown in FIG. 8. Resistive heating elements 35 are positioned in the end section 30 adjacent installed capsule 15. The heating elements 35 are in electrical communication with electrical power supply 37 (batteries in FIG. 8 but AC corded power is also usable). The dispenser 11a includes a switch 38 for supplying electrical power to the heating elements 35 for generating heat adjacent the capsule 15 to heat up the material in the capsule 15 before expressing the resins from the capsule 15. Heating the paste composite resin allows a more highly filled composite (e.g., paste) to be expressed through the tip of the capsule 15.

Figure 9:
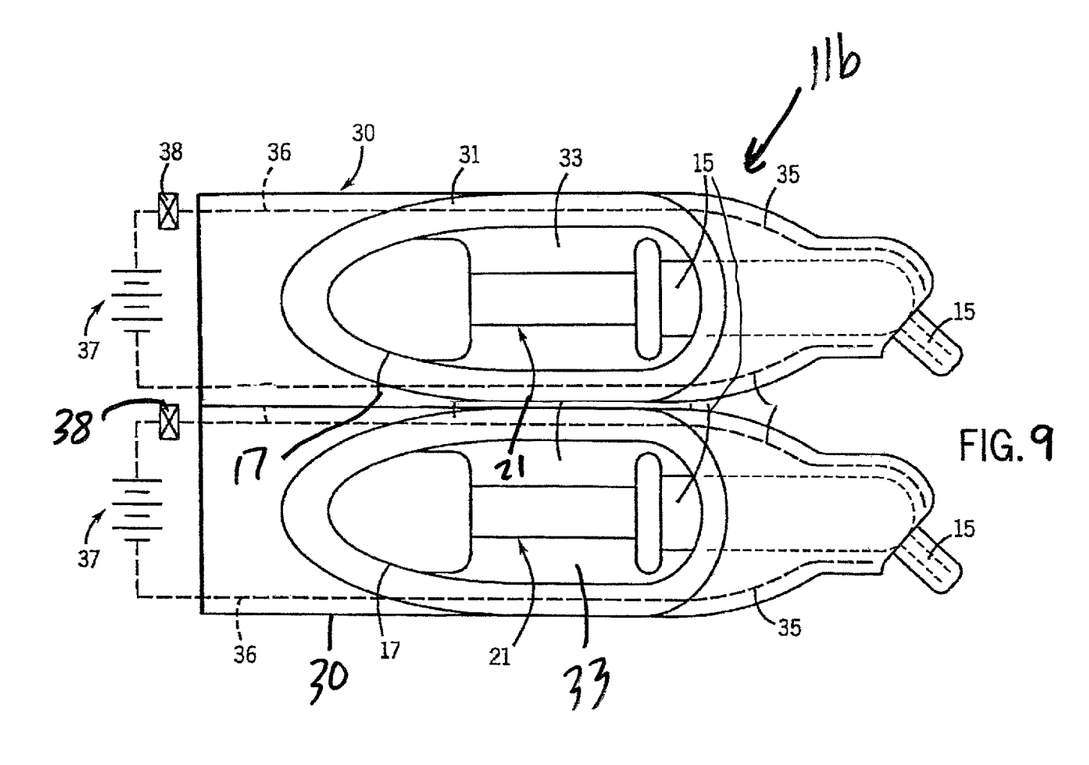
FIG. 9 shows a view similar to FIG. 8 showing another version of a composite dispenser having means for heating two capsules of FIGS. 4-6 and/or FIG. 7.

Turning now to FIG. 9, there is shown another non-limiting example dental composite dispenser 11b according to the invention. The dental composite dispenser 11b includes a pair of housing end sections 30 for dispensing resins from two separate capsules 15. Each piston 17 drives a rubber plunger 21 which in turn presses the resin materials from the capsules 15 as described above for dispenser 11a. The end sections 30 each have an opening 31 defining a space 33 in which the separate capsules 15 may be inserted into place as shown in FIG. 9. Resistive heating elements 35 are positioned in the end sections 30 adjacent installed capsules 15. The heating elements 35 are in electrical communication with electrical power supplies 37 (batteries in FIG. 9 but AC corded power is also usable). The dispenser 11b includes switches 38 for supplying electrical power to the heating elements 35 for generating heat adjacent the capsules 15 to heat up the material in the capsules 15 before expressing the resins from the capsules 15.

In an example use of the dental composite dispenser 11b, one capsule 15 includes a light curable resin tooth bonding agent 125 that is first extruded from the capsule 15. The other capsule 15 includes a second (flowable) composite resin filling material 24 and a first (paste) composite resin composite material 23 that are thereafter sequentially extruded from the other capsule 15. Alternatively, separate rubber plungers 21 may first extrude the light curable resin tooth bonding agent 125 from a first compartment of a capsule and then sequentially extrude the second (flowable) composite resin filling material 124 and the first (paste) composite resin material 123 from a second compartment of the same capsule 15.

The paste composite resin filling material 123 and the flowable composite resin filling material 124 may include a polymerizable (e.g., light curable) resin and a filler. Non-limiting examples of suitable resins include acrylate resins, methacrylate resins, and silorane-based resins. Non-limiting examples of suitable fillers include silica, silicate glass, quartz, barium silicate, strontium silicate, barium borosilicate, strontium borosilicate, borosilicate, lithium silicate, lithium alumina silicate, amorphous silica, calcium phosphate, alumina, zirconia, tin oxide, and titania. The paste composite can include greater than 30% by volume filler, or greater than 40% by volume filler, or greater than 50% by volume filler, or greater than 60% by volume filler, or greater than 70% by volume filler, or greater than 80% by volume filler, or greater than 90% by volume filler. Preferably, the dental restorative material (a combination of the first paste composite resin material and the second flowable composite resin filling material) has a volume shrinkage of 3% or less upon curing, More preferably, the dental restorative material has a volume shrinkage of 2% or less upon curing. Most preferably, the dental restorative material has a volume shrinkage of 1% or less upon curing.

Various dental matrices may be used with the invention. Each matrix can be tooth specific, or the matrix can be tooth type specific, or the matrix can be tooth surface specific. By "tooth specific" it is meant that the matrix is configured to conform to the shape of the outer surface of the specific natural tooth being restored such as (without limitation) an upper left central incisor. By "tooth type specific" it is meant that the matrix is configured to conform to the shape of the outer surface of the specific type of natural tooth being restored such as (without limitation) an upper incisor. By "tooth surface specific" it is meant that the matrix is configured to conform to the shape of the outer surface of the specific natural tooth surface being restored such as (without limitation) an upper left incisor mesial surface.

Figure 10:
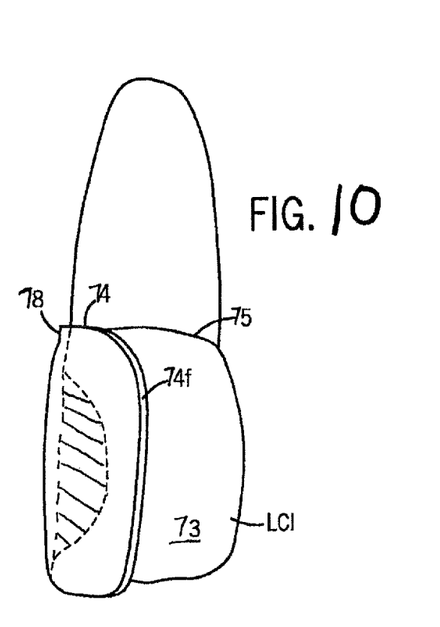
FIG. 10 is a front view showing a sectional type matrix on the left central incisor.

In FIG. 10, a non-limiting example universal sectional type matrix 74 for use with the invention on anterior teeth is shown. The matrix 74 has a root-crown interface 78 and a side terminal flange 74f that extends away from the surface of the left central incisor (LCI) tooth when the matrix 74 is placed on the LCI tooth. The matrix 74 can be translucent, sectional, and/or anatomically shaped. The matrix 74 as shown is partially anatomic (i.e., it is less than all anatomic). However, a fully anatomic matrix is also in accordance with the invention. By "anatomic", it is meant that the matrix has an inner surface that conforms to the shape of the outer surface of the region of the natural tooth being restored. A matrix used with the invention can be anatomically shaped such that the matrix is hands free and self stabilizing (i.e., there is no requirement for a matrix stabilizer that conforms the matrix to the tooth).

Figure 11:
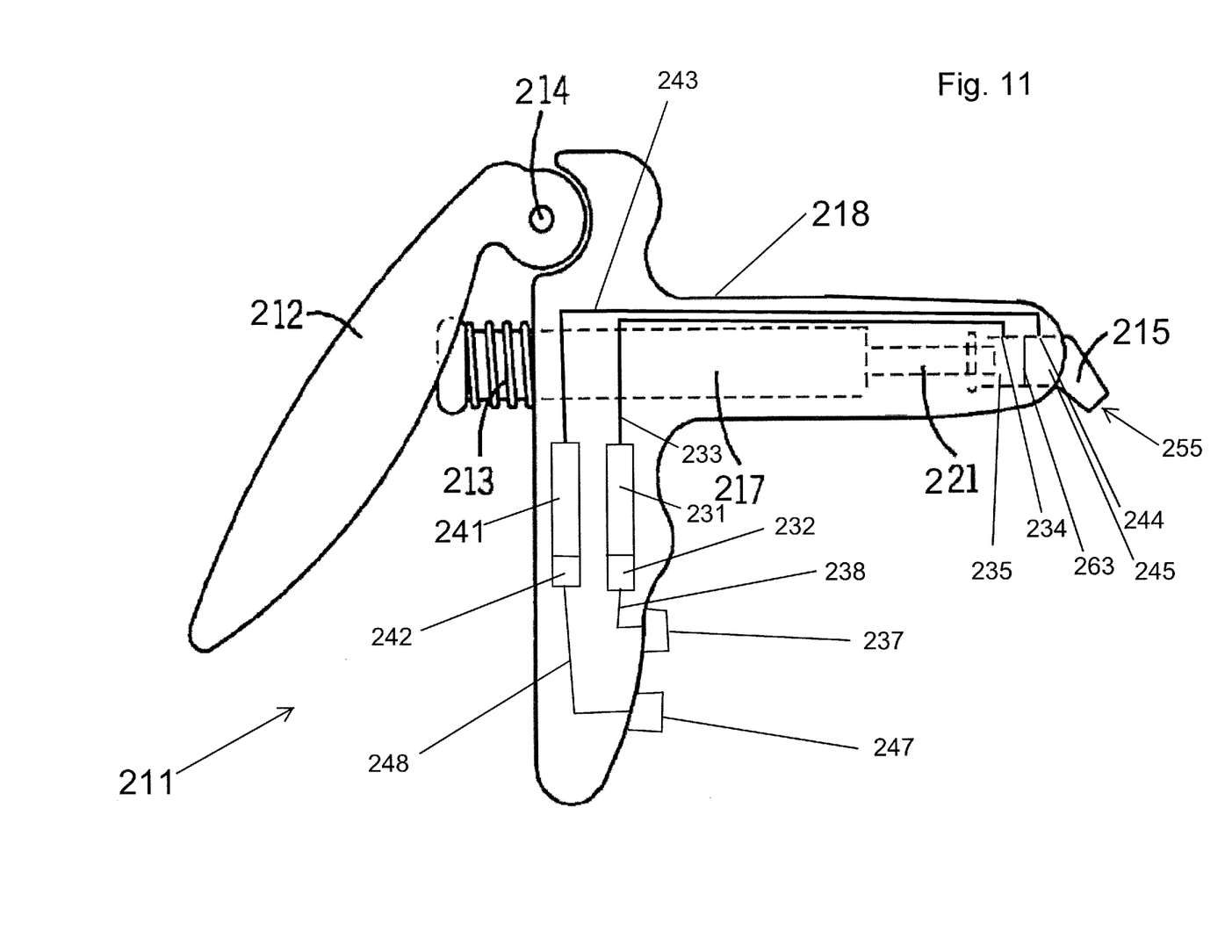
FIG. 11 is a side view of another embodiment of a composite dispenser according to the invention from which composite resin filling materials are dispensed.

In FIG. 11, there is shown another non-limiting example dental composite dispenser of the invention. The dental composite dispenser 211 has a chamber 215 in which resin composite filling materials are loaded. A piston 217 in the dispenser housing 218 drives a rubber plunger 221 which in turn presses the composite resin filling material. The handle 212 of the dispenser 211 is pressed and compresses a spring 213. A hinge 214 allows rotation of the handle 212 to press the piston 217.

In the dispenser housing 218 of the dispenser 211, there is located a first composite reservoir 231 for containing a first composite (e.g., paste) resin filling material and a second composite reservoir 241 for containing a second composite (e.g., flowable) resin filling material. A first pump 232 moves the first composite resin filling material from the first composite reservoir 231 via a conduit 233 through a one-way valve 234 and into a proximal end 235 of the chamber 215. A first switch 237 in electrical communication via a line 238 with the first pump 232 turns the first pump 232 on and off. A second pump 242 moves the second composite resin filling material from the second composite reservoir 241 via a conduit 243 through a one-way valve 244 and into a distal end 245 of the chamber 215. A second switch 247 in electrical communication via a line 248 with the second pump 242 turns the second pump 242 on and off.

The use of separate reservoirs 231, 241, pumps 232, 242 and switches 237, 247 allows for different delivery methods for the first (paste) composite resin filling material and the second (flowable) composite resin filling material. In one delivery method, the user simultaneously or separately presses the first switch 237 and the second switch 247 thereby delivering the first (e.g., paste) composite resin material into the proximal end 235 of the chamber 215 and the second (e.g., flowable) composite resin filling material into the distal end 245 of the chamber 215. The second (flowable) composite resin filling material is then first extruded from a dispensing orifice 255 of the chamber 215 as the plunger 221 is driven into the barrel of the chamber 215 and pressure is applied to the first (paste) composite resin filling material which thereby applies pressure to the second (flowable) composite resin filling material. Further plunger pressure next extrudes the first (paste) composite resin filling material from the dispensing orifice 255 of the chamber 215. Thus, the second (flowable) composite resin filling material and the first (paste) composite resin composite material are sequentially extruded from the capsule 215. Optionally, a movable barrier 263 can be positioned between the proximal end 235 and the distal end 245 of the chamber 215 when delivering the first (paste) composite resin filling material and the second (flowable) composite resin filling material to the chamber 215. The barrier 263 is moved out of the way during extruding. An armature of an electromechanical solenoid can be attached to the barrier 263 for moving the barrier 263.

In another delivery method of the dispenser 211, the user first presses the second switch 247 thereby delivering the second (flowable) composite resin filling material into the chamber 215. The second (flowable) composite resin filling material is then extruded from the dispensing orifice 255 of the chamber 215 as the plunger 221 is driven into the barrel of the chamber 215 and pressure is applied to the second (flowable) composite resin filling material. The user then presses the first switch 237 thereby delivering the first (paste) composite resin filling material into the chamber 215. The first (paste) composite resin filling material is then extruded from the dispensing orifice 255 of the chamber 215 as the plunger 221 is driven into the barrel of the chamber 215 and pressure is applied to the first (paste) composite resin filling material. Thus, the second (flowable) composite resin filling material and the first (paste) composite resin composite material are separately sequentially extruded from the capsule 215.

Thus, the invention provides methods for the restoration of a decayed portion of a tooth or re-restoration of a previously filled tooth, and also provides dental capsules and composite resin dispensers that may be used in the methods for the restoration of a decayed portion of a tooth Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A capsule for use in a dental composite dispenser, the capsule comprising: a hollow body comprising a wall defining an interior space of the body, the body including a proximal end and a distal end having a dispensing orifice; a first composite resin positioned in the interior space of the body; and a second composite resin positioned in the interior space of the body, wherein the first composite resin has a first viscosity, the second composite resin has a second viscosity less than the first viscosity, wherein no barrier is positioned between the first composite resin and the second composite resin, and wherein the wall is continuous from the proximal end to the distal end, and wherein a first longitudinal axis of the dispensing orifice is angled relative to a second longitudinal axis of the proximal end, wherein the second composite resin is configured to be extruded through the dispensing orifice prior to the first composite resin, and wherein the first composite resin and the second composite resin are in contact before use of the capsule in the dental composite dispenser.

2. The capsule of claim 1 wherein:
the second composite resin is positioned between the first composite resin and the dispensing orifice.

3. The capsule of claim 1 further comprising:
a plunger positioned between the first composite resin and the proximal end of the body.

4. The capsule of claim 1 wherein:
the first composite resin is a paste composite, and
the second composite resin is a flowable composite.

5. The capsule of claim 4 wherein:
the first composite resin comprises from about 1% by volume to about 99% by volume of the interior space of the body, and
the second composite resin comprises from about 1% by volume to about 99% by volume of the interior space of the body.

6. The capsule of claim 4 wherein:
the first composite resin comprises from about 25% by volume to about 99% by volume of the interior space of the body, and
the second composite resin comprises from about 1% by volume to about 75% by volume of the interior space of the body.

7. The capsule of claim 4 wherein:
the first composite resin comprises from about 50% by volume to about 99% by volume of the interior space of the body, and
the second composite resin comprises from about 1% by volume to about 50% by volume of the interior space of the body.

8. The capsule of claim 4 wherein:
the first composite resin comprises from about 65% by volume to about 85% by volume of the interior space of the body, and
the second composite resin comprises from about 15% by volume to about 35% by volume of the interior space of the body.

9. The capsule of claim 1 wherein:
the first composite resin and the second composite resin are essentially not mixed before exiting the dispensing orifice.

10. The capsule of claim 1 wherein:
less than about 5% by volume of the first composite resin and less than about 5% by volume of the second composite resin are mixed before exiting the dispensing orifice.

11. The capsule of claim 1 wherein:
less than about 10% by volume of the first composite resin and less than about 10% by volume of the second composite resin are mixed before exiting the dispensing orifice.

12. The capsule of claim 1 further comprising:
a light-curable resin tooth bonding agent positioned in the interior space of the body between the second composite resin and the dispensing orifice.

13. The capsule of claim 1, wherein the second composite resin is light curable.

14. The capsule of claim 1 wherein:
the first composite resin is a paste composite, and
the viscosity of the first composite resin can be lowered by heating.

15. The capsule of claim 1 wherein:
an amount of second filler in the second composite resin is 20 to 25 percent less than an amount of first filler in the first composite resin.

16. The capsule of claim 1 wherein:
the first composite resin is a bulk fill paste composite, and
the second composite resin is a bulk fill flowable composite.

17. The capsule of claim 1 wherein:
the first composite resin is a resin modified glass ionomer composite, and
the second composite resin is a resin modified glass ionomer composite.

18. The capsule of claim 1 wherein:
the capsule is a single use, disposable capsule.

19. The capsule of claim 1, wherein:
the first composite resin is a dental restorative material; and
the second composite resin is a dental restorative material.

20. A capsule comprising: a hollow body comprising a wall defining an interior space of the body, the wall being continuous from a proximal end of the body to a distal end of the body, the hollow body defining a dispensing orifice, a first longitudinal axis of the dispensing orifice is angled relative to a second longitudinal axis of the proximal end;
a first dental composite resin positioned in the interior space of the body, the first dental composite having a first viscosity;

a second dental composite resin positioned in the interior space of the body, the second dental composite resin having a second viscosity less than the first viscosity;

a light-curable resin tooth bonding agent positioned in the interior space of the body between the second composite resin and a dispensing orifice;

a frangible barrier positioned in the interior space of the body between the second dental composite resin and the light-curable resin tooth bonding agent.

21. A capsule comprising: a hollow body comprising a wall defining an interior space of the body; a first dental composite resin positioned in the interior space of the body, the first dental composite having a first viscosity; and a second dental composite resin positioned in the interior space of the body, the second dental composite resin having a second viscosity less than the first viscosity, the second dental composite resin being light curable, and the second composite resin is configured to be extruded through a dispensing orifice of the capsule prior to the second first composite resin and no barrier is positioned between the first composite resin and the second composite resin.

22. The capsule of claim 21, wherein the first dental composite is light curable.

* * * * *

UNITED STATES PATENT AND TRADEMARK OFFICE
CERTIFICATE OF CORRECTION

PATENT NO. : 11,351,009 B2
APPLICATION NO. : 15/533220
DATED : June 7, 2022
INVENTOR(S) : David J. Clark and Jeremy Henderson It is certified that error appears in the above-identified patent and that said Letters Patent is hereby corrected as shown below:

In the Claims

Claim 21, Column 13, Line 19, "dispensing orifice of the capsule prior to the second first" should be --dispensing orifice of the capsule prior to the first--.

Signed and Sealed this
Twenty-sixth Day of March, 2024

Katherine Kelly Vidal
*Director of the United States Patent and Trademark Office*